US010113958B2

(12) United States Patent
Perkins

(10) Patent No.: US 10,113,958 B2
(45) Date of Patent: Oct. 30, 2018

(54) OPTICALLY TRANSPARENT FILMS FOR MEASURING OPTICALLY THICK FLUIDS

(71) Applicant: Halliburton Energy Services, Inc., Houston, TX (US)

(72) Inventor: David L. Perkins, The Woodlands, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 318 days.

(21) Appl. No.: 14/441,481

(22) PCT Filed: Dec. 28, 2012

(86) PCT No.: PCT/US2012/072193
§ 371 (c)(1),
(2) Date: May 7, 2015

(87) PCT Pub. No.: WO2014/105070
PCT Pub. Date: Jul. 3, 2014

(65) Prior Publication Data
US 2015/0293016 A1   Oct. 15, 2015

(51) Int. Cl.
*G01N 33/28* (2006.01)
*G01J 3/46* (2006.01)
(Continued)

(52) U.S. Cl.
CPC ........... *G01N 21/3577* (2013.01); *C25D 5/10* (2013.01); *C25D 5/12* (2013.01); *C25D 5/48* (2013.01);
(Continued)

(58) Field of Classification Search
CPC ...... C25D 5/10; E21B 49/08; G01N 21/0303; G01N 21/031; G01N 21/31; G01N 21/3577; G01N 21/39; G01N 2201/0668
(Continued)

(56) References Cited

U.S. PATENT DOCUMENTS 6,147,756 A * 11/2000 Zavracky .................. G01J 3/26
356/519
6,903,823 B1   6/2005 Muller et al.
(Continued)

FOREIGN PATENT DOCUMENTS

EP           0515905 A2    12/1992
WO    WO 2001/020294       3/2001
WO    WO 2005/062986 A2    7/2005

OTHER PUBLICATIONS

Partial Supplementary European Search Report issued for EP 12890996 dated Sep. 16, 2016.
(Continued)

*Primary Examiner* — Sunghee Y Gray
(74) *Attorney, Agent, or Firm* — Haynes and Boone, LLP

(57) ABSTRACT

A multilayered film and a method for performing spectroscopic measurements in a fluid are provided. The multilayered film includes a substrate; a porous layer adjacent to the substrate; and a reflective layer formed on the porous layer, wherein the porous layer selectively allows a component of a fluid to be optically measured when the multilayered film is immersed in the fluid. A sensor for spectroscopic measurements in crude oil samples including a multilayered film as above is also provided. A method of manufacturing a multilayered film for spectroscopic measurements in fluids as above is also provided.

14 Claims, 14 Drawing Sheets

(51) Int. Cl.
*C25D 5/00* (2006.01)
*G01N 21/3577* (2014.01)
*E21B 49/08* (2006.01)
*G01N 21/31* (2006.01)
*C25D 5/10* (2006.01)
*C25D 5/12* (2006.01)
*C25D 5/48* (2006.01)
*C25D 5/52* (2006.01)
*C25D 7/00* (2006.01)
*C25D 9/04* (2006.01)
*G01N 21/39* (2006.01)
*G01N 21/03* (2006.01)

(52) U.S. Cl.
CPC ............... *C25D 5/52* (2013.01); *C25D 7/00* (2013.01); *C25D 9/04* (2013.01); *E21B 49/08* (2013.01); *G01N 21/31* (2013.01); *G01N 21/39* (2013.01); *G01N 33/2823* (2013.01); *G01N 21/031* (2013.01); *G01N 21/0303* (2013.01); *G01N 2201/0612* (2013.01); *G01N 2201/0668* (2013.01)

(58) Field of Classification Search
USPC ........................ 205/112, 81; 356/402, 70
See application file for complete search history.

(56) References Cited

U.S. PATENT DOCUMENTS

| | | | |
|---|---|---|---|
| 7,808,632 | B2 | 10/2010 | Vaidya et al. |
| 7,889,346 | B2 | 2/2011 | Myrick et al. |
| 2007/0166761 | A1 | 7/2007 | Moore |
| 2008/0008625 | A1 | 1/2008 | Thomas et al. |
| 2008/0231849 | A1* | 9/2008 | Myrick ............... G01N 21/45 356/300 |
| 2009/0140144 | A1 | 6/2009 | Myrick et al. |
| 2009/0152664 | A1* | 6/2009 | Klem ............... H01L 27/14603 257/440 |
| 2009/0166037 | A1 | 7/2009 | Sroka |
| 2009/0250613 | A1 | 10/2009 | Myrick et al. |
| 2009/0314339 | A1* | 12/2009 | Hayase ............... H01G 9/2022 136/256 |
| 2010/0277740 | A1 | 11/2010 | Hulteen et al. |
| 2011/0199610 | A1 | 8/2011 | Myrick et al. |
| 2013/0188169 | A1* | 7/2013 | Harrison ............... G01N 21/85 356/36 |
| 2013/0284895 | A1* | 10/2013 | Freese ............... G02B 27/1006 250/208.2 |

OTHER PUBLICATIONS

International Search Report and the Written Opinion of the International Searching Authority, or the Declaration, dated Sep. 4, 2013, PCT/US2012/072193, 12 pages, ISA/KR.

Miney et al., "A New Optically Reflective Thin Layer Electrode (ORTLE) Window: Gold on a Thin Porous Alumina Film Used to Observe the Onset of Water Reduction," Electroanalysis, 2004, vol. 16.

* cited by examiner

OPTICALLY TRANSPARENT FILMS FOR MEASURING OPTICALLY THICK FLUIDS

The present application is a U.S. National Stage patent application of International Patent Application No. PCT/US2012/072193, filed on Dec. 28, 2012, the benefit of which is claimed and the disclosure of which is incorporated herein by reference in its entirety.

BACKGROUND

1. Technical Field

Embodiments disclosed herein relate to the field of thin film optical devices for spectroscopic measurements of a fluid. In particular, embodiments disclosed herein relate to multilayered films for spectroscopic measurements of optically thick fluids.

2. Description of Related Art

In the field of oil exploration and extraction there is often the need to perform measurements of fluid samples that are optically thick, or opaque. Optical Density (OD) is a property of a material that measures the attenuation of light of a certain wavelength traversing through a portion of the material. The OD or opaqueness of a material is due to absorption and scattering of the light by molecules forming the material. Examples of wavelength dependent light absorbing phenomena are electronic transitions (visible) and vibration and rotational modes (near-infrared and mid-infrared) of the materials in the sample. Scattering of light arises from interactions with particles in a system in which the path of the light is changed. Scattering can be categorized in three general types (Rayleigh, Mie, and geometric), dependent on the size of the particle relative to the incident wavelength of light. In the area of hydrocarbon exploration, production, and processing, scattering of light arises from the presence of larger components or macromolecular structures, such as condensates and other particulates included in the fluids. Optical measurement techniques are useful because, in a non-invasive manner, the chemical composition of a sample may be obtained through the material absorption properties at selected wavelengths.

State-of-the-art optical measurement techniques are difficult to apply in hydrocarbon exploration and extraction due to the opaque nature of crude oil samples for a broad spectral wavelength region, covering from the visible and near infrared (400 nm-2500 nm) to the mid-infrared and beyond (3500 nm-10 µm). Moreover, the high OD of fluid samples in the oil industry includes scattering from particulates such as asphaltenes and other extraneous components included in the fluid. In many instances large particulates and components may not be of interest for a measurement, since they may be easily removed from the fluid at a later stage in refinement. Another problem encountered in crude oil samples is that the many analytes of interest within the sample may have considerably different contributions to the OD of the sample. Thus, in many instances, an analyte having a low absorptivity is 'masked out' by analytes having a high absorptivity. For example, a small optical path length may result in considerable light absorption for a first analyte, while resulting in absorption that is barely detectable for a second analyte. Traditional spectroscopic measurements may also have the problem of highly absorbing samples being 'masked out' by an optical path length that may be too long. Thus, a component of light having certain wavelength may be completely or almost completely absorbed by an analyte before the light goes through the sample, impeding determination of analyte concentration. The ability of an optical system to measure a plurality of analytes in a sample having a wide range of absorptivity is referred to as 'dynamic range' of the system.

What is needed is a device and a method to allow spectral measurements of optically thick fluids, like crude oils, having a wide dynamic range.

BRIEF SUMMARY

A multilayered film for spectroscopic measurements in a fluid according to embodiments herein may include a substrate; a porous layer adjacent to the substrate; and a reflective layer formed on the porous layer, wherein the porous layer selectively allows a component of a fluid to be optically measured when the multilayered film is immersed in the fluid.

A sensor for spectroscopic measurements in crude oil samples according to embodiments disclosed herein may include a multilayered film including: a substrate; a porous layer adjacent to the substrate; and a reflective layer formed on the porous layer, wherein the porous layer selectively allows a component of a fluid to be optically measured when the multilayered film is immersed in the fluid; a light illumination system to direct an input light to the multilayer film; and a light detection system to detect a light from the multilayer film.

According to some embodiments, a method for measuring properties of a fluid may include directing an input light through a substrate of a multilayered film, the multilayered film including a porous layer and a reflective layer disposed on the porous layer; detecting an output light from the substrate; and comparing the output light with the input light to measure a property of at least one component of the fluid.

According to some embodiments, a method of manufacturing a multilayered film for spectroscopic measurements in fluids may include cleaning an optically transparent substrate; forming an aluminum layer on the optically transparent substrate; applying a voltage to the substrate in a phosphoric acid solution to form a porous alumina layer; and forming a reflective layer having a selected thickness on a surface of the porous alumina layer.

These and other embodiments will be described in further detail below, with reference to the following drawings.

BRIEF DESCRIPTION OF THE DRAWINGS

Wherever possible, the same reference numbers are used throughout the drawings to refer to the same or like elements.

DETAILED DESCRIPTION

Figure 1:
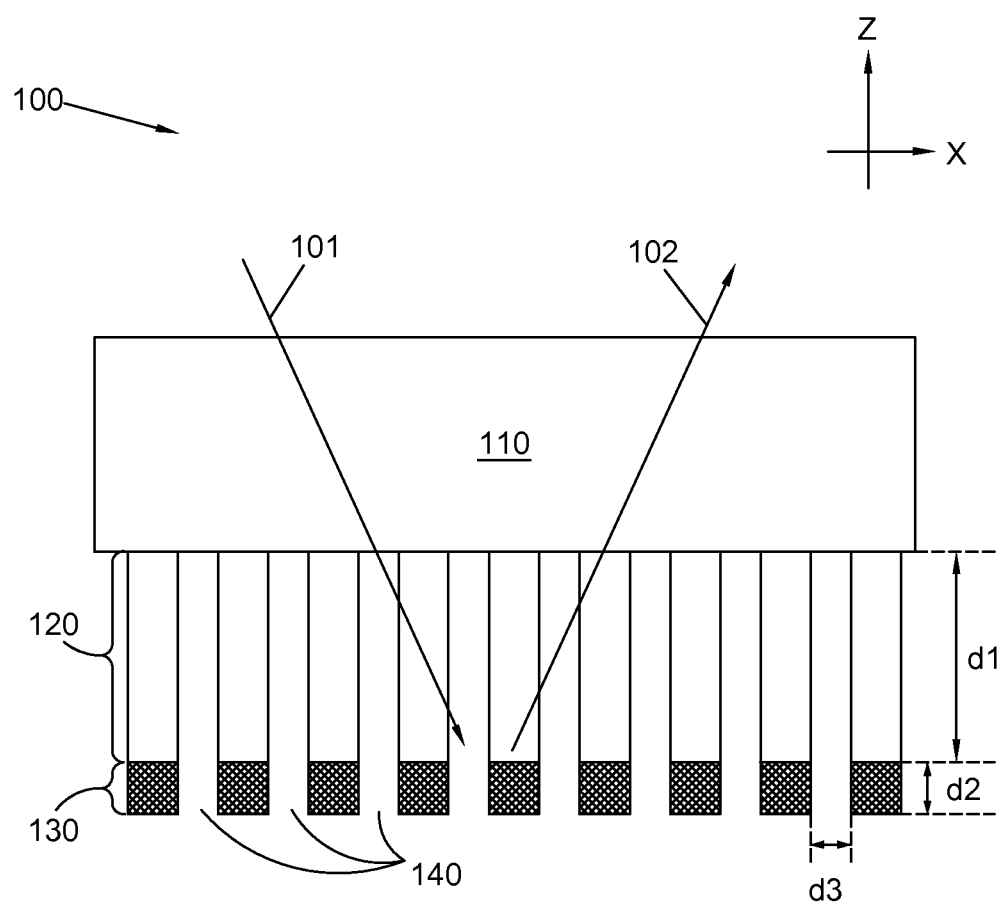
FIG. 1 shows a multilayered film for measuring optically thick fluids, according to some embodiments.

Optical absorption measurement techniques include measuring an output signal intensity '$I_{out}$' and comparing it to an input signal intensity '$I_{in}$'. The signal intensity '$I_{out}$' may be the intensity of an input signal '$I_{in}$' traversing a thickness of a sample, or optical path. The output signal may be measured in transmittance or reflectance mode. According to the Beer-Lambert law of absorption, for a monochromatic light beam having wavelength '$\lambda$' and a negligible cross-section, the relation between $I_{out}(\lambda)$ and $I_{in}(\lambda)$ is given by $$I_{out}(\lambda) = I_{in}(\lambda) \cdot 10^{-A(\lambda)} \quad (1)$$

In Eq.(1), the absorbance $A(\lambda)$ is a property of the material and the optical setup, including an optical path length '$l(\lambda)$' (usually in cm), and a concentration '$C$' of the analyte absorbing radiation at a wavelength, $\lambda$. The transmittance, $T_\lambda$, of a material is given as the ratio of $I_{out}(\lambda)/I_{in}(\lambda)$ (cf. Eq.(1)). The absorbance $A(\lambda)$, in Eq. (1) may be written as $$A(\lambda) = \varepsilon(\lambda) \cdot l(\lambda) \cdot C \quad (2)$$

where $\varepsilon(\lambda)$ is the molar absorptivity ($mol^{-1} \cdot cm^2$) of the analyte and C is the molar concentration in the fluid or sample ($mol/cm^3$). The optical density (OD) of a material is measured in a base 10 logarithmic scale, similar to Eq.(1)

$$I_{out}(\lambda) = I_{in}(\lambda) \cdot 10^{-OD} \quad (3)$$

Thus, in some embodiments, the OD of a material is approximately the same as the absorbance (cf. Eqs. (1) and (2)). While a definition of an 'optically thick' material is relative and depends on geometrical factors such as path length and wavelength, an OD of 3 or more is considered a high optical density.

According to embodiments disclosed herein, optically transparent porous films of controllable sub-micron (1 micron=1 μm=1×10$^{-6}$ meters) thickness allow measurement of properties of optically thick fluids. An optically thick fluid is an opaque fluid having a large Optical Density (OD>3). Optical measurements in optically thick fluids are difficult with traditional optical sampling methods due to low signal intensity. The low signal is due to low transmittance through the fluid. In some embodiments a low transmittance may lead to low reflectivity in measurement systems where an incident beam is reflected after transmission through a layer of fluid sample.

Devices fabricated according to embodiments disclosed herein allow sampling of fluids that are optically thick and contain suspended solids. In some embodiments, suspended solids and particulates are prevented from obstructing the flow of the fluid through the optical system. Further according to some embodiments, suspended solids and particulates are prevented from contaminating optical elements in a measurement system. Also, embodiments of a multilayered film for optical measurements as disclosed herein reduce spurious scattering effects induced by suspended solids and particulates in the fluid. Thus, some embodiments of multilayered films as disclosed herein eliminate scattering interference in absorption measurements. Embodiments of a multilayered film as disclosed herein are simple to manufacture and easily integrated to existing fluid systems.

FIG. 1 shows a multilayered film 100 for measuring optically thick fluids, according to some embodiments. Film 100 includes an optically transparent substrate 110, a porous layer 120 having a thickness d1, and a reflective layer 130 having a thickness d2. Porous layer 120 includes pores 140 having a diameter $d_3$. Substrate 110 may be formed of a material that is transparent for a wavelength region of interest for the measurements. For example, substrate 110 may be made of a glass or a crystal transparent in the visible and near infrared wavelength region from about 400 nanometers ("nm") to about 2500 nm of wavelength (1 nanometer=1×10$^{-9}$ meters). In some embodiments, substrate 110 may be made of sapphire to extend the measurement into the mid-infrared wavelength region. According to some embodiments, porous layer 120 may act as a filter to keep larger particulates outside of the optically sensitive area in multilayered film 100. In some embodiments, substrate 110 may be constructed as a multilayered substrate designed to impart a wavelength dependent change in the intensity of incident light 101 as it is reflected or transmitted through multilayered film 100. Furthermore, in some embodiments porous layer 120 has a thickness $d_1$ that provides a reduced path length for absorption measurements of small particulates and molecules passing through the pores. For example, in some embodiments thickness d1 may be less than 1 μm. In some embodiments, d1 may be a few hundred nanometers, such as from about 500 nm, or up to about 800 nm. According to some embodiments, porous layer 120 is coated with an optically reflective material, for example gold, which does not close the opening of the pores, to form reflective layer 130. Thus, in some embodiments reflective layer 130 is formed on porous layer 120.

Porous layer 120 allows passive filtration of the analytical solution to be interrogated. Thus, porous layer 120 selectively allows a component of a fluid to be optically measured when multilayered film 100 is immersed in a fluid. Reflective layer 130 reflects incident light 101 into output light 102 to be measured by an optical system. Reflective layer 130 allows for electrochemical measurements in a sample by using reflective layer 130 as an electrode and applying a voltage. In some embodiments, passing a current through a reflective layer 130 made of a conducting material allows heating, which may be used for cleaning (burning off debris) or temperature control for the sample.

Filtration through pores 140 eliminates or significantly reduces undesired scattering of light by not allowing particulates and contaminants larger than a pore diameter, $d_3$, from the bulk fluid to enter pores 140 in porous layer 120. (Although the term "diameter" is used, it is understood that the pores 140 are not limited to a circular cross section, but may take a variety of shapes.) Pores 140 are not sealed by reflective layer 130. Thus, pores 140 may be filled with analytes included in the optically thick fluid. Pore diameter $d_3$ is small enough to filter particulates suspended in the fluid out of porous layer 120. In some embodiments pore diameter $d_3$ may range from about 50 nm to about 200 nm. For example, the pore diameter $d_3$, on average, may be approximately 100 nm. Pore diameter $d_3$ allows fluid particles having smaller dimensions to enter the filtering layer, for absorption measurements. In some embodiments, pore diameter d3 may be selected to filter large particulates such as asphaltenes in a crude oil sample, out of porous layer 120. Crude oil may be oil extracted from a drilling platform, before any treatment or processing such as filtering, heating, or condensing, is applied to the oil.

The fluid filling porous layer 120 receives incident light 101, measured as output light 102. In some embodiments output light 102 may be reflected off of reflective layer 130 in multilayered film 100, after traversing twice through a thickness $d_1$ of porous layer 120. The thickness $d_2$ of reflective layer 130 is such that input beam 101 is reflected into output beam 102 for a wide range of wavelengths. For example, in embodiments where reflective layer 130 is made of gold, thickness $d_2$ may be from about 100 nm to about 200 nm, and reflect input beam 101 at wavelengths from the visible to mid IR (400 nm-10 μm). Porous layer 120 is filled with absorbing analytes of interest for an optical measurement, when multilayered film 100 is placed in contact with a fluid. Incident light beam 101 is brought into substrate 110 from a side of multilayered film 100 opposite to the side in contact with the fluid. In some embodiments, reflective layer 130 is in contact with the fluid.

A multilayered film 100 allows optical sampling of native down-hole reservoir fluids in oil exploration and extraction applications. In such embodiments, a crude oil sample may include numerous insoluble scattering particulates like silt, mud, drilling fluid, and asphaltenes, or the like, which may be filtered out of the optical measurement device by pores 140.

In some embodiments, reflective film layer 130 may be an electrically conductive layer used as an electrode in electrochemical redox reactions. For example, reflective layer 130 may be one of three electrodes used for electrochemical spectroscopy. In some embodiments, by applying a voltage across reflective layer 130 multilayered film 100 is resistively heated, allowing particulates and/or residues to be cleaned from its surface. In some embodiments, reflective layer 130 is resistively heated to allow temperature control of multilayered film 100 and the analyte contained in pores 140.

Multilayered film 100 may provide a short path length 'l' for spectroscopic measurements of an analyte in an optically thick fluid, the analyte having a high molar absorptivity $\varepsilon(\lambda)$, and even having a large concentration, C. By significantly reducing the path length 'l(λ)' in porous layer 120, the OD for input beam 101 may be low enough to provide a measurable output beam 102. Furthermore, the path length of input beam 101 at the wavelength of interest may be such that a reduced OD results in an approximately linear expression for Eqs. (1) and (2)

$$I_{out}(\lambda) \approx I_{in}(\lambda) \cdot (1 - \kappa \varepsilon(\lambda) \cdot l(\lambda) \cdot C) \quad (4)$$

where $\kappa = \log_{10} e$.

Eq.(4) may be rewritten in terms of the ratio $1/T_\lambda$ to obtain a linear relation with a positive slope, as $$\frac{1}{T_\lambda} = \frac{I_{in}(\lambda)}{I_{out}(\lambda)} \approx \cdot 1 + \kappa \varepsilon(\lambda) \cdot l(\lambda) \cdot C = 1 + \kappa \cdot A(\lambda) \quad (5)$$

A linear relation between $1/T_\lambda$ and absorbance $A_\lambda$ as expressed in Eq. (5) may be obtained for an analyte having a molar absorptivity $\varepsilon(\lambda)$ that is very low, an analyte having very low concentration C, or a combination of a short optical path $l(\lambda)$, a low molar absorptivity $\varepsilon(\lambda)$, and a low concentration C. Equations 4 and 5 are valid typically in embodiments such that $A(\lambda)$ has a value less than 1, such as 0.1 or lower.

The length of the pores $d_1$ in porous layer 120 is controlled by the process in which porous layer 120 is made. Therefore, the optical path length l(4 through porous layer 120 can be controlled by design. Embodiments consistent with the present disclosure may include porous layers 120 having path lengths shorter than 1 mm (=0.001 meter), with accuracy and reproducibility within 1 micron, or less. A short optical path reduces the optical density of a sample and allows measurements of fluids including analytes having large molar absorptivity. Furthermore, embodiments of multilayered film 100 avoid high optical densities resulting from scattering. Scattering effects are suppressed by filtering large particulates out of the optically sensitive area in porous layer 120.

Figure 2:
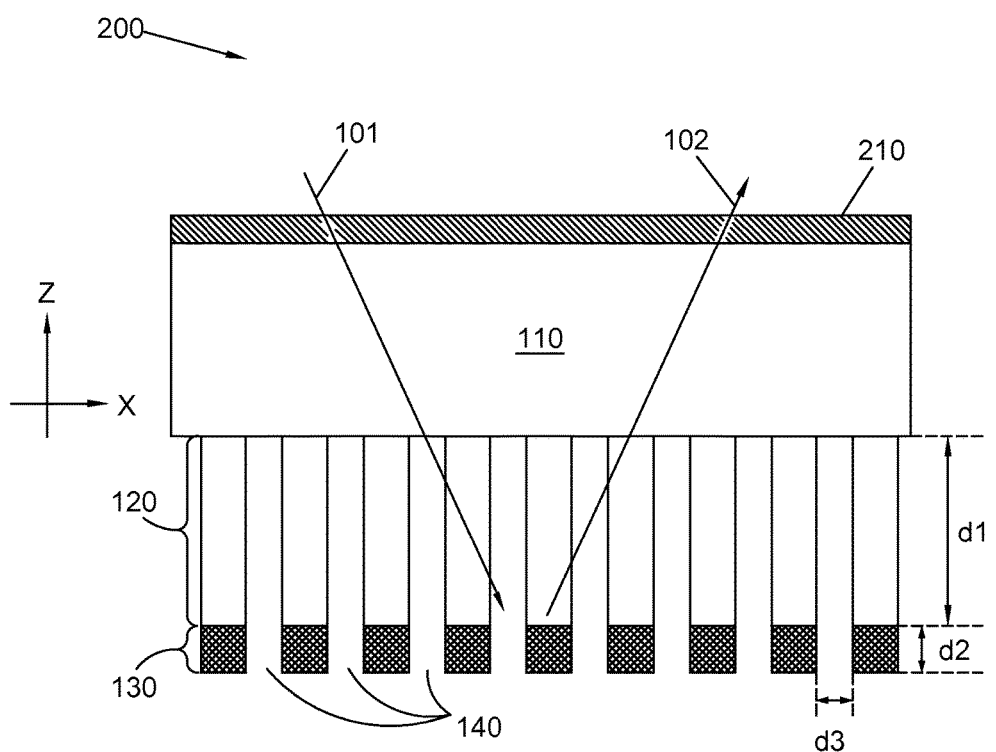
FIG. 2 shows a multilayered film for measuring optically thick fluids, according to some embodiments.

FIG. 2 shows a multilayered film 200 for measuring optically thick fluids, according to some embodiments. Film 200 includes optically transparent substrate 110, porous layer 120, and reflective layer 130 having pores 140 as described in detail above (cf. FIG. 1). Film 200 may also include a multivariate optical element (MOE) layer 210. According to some embodiments, layer 210 is an integrated computational element (ICE), including multiple film layers having selected thicknesses. Thus, ICE 210 may be deposited on transparent substrate 110 on a surface opposite porous layer 120.

According to some embodiments, ICE 210 may be designed to have spectral properties such that when output beam 102 creates a signal in a photo detector, the signal has a voltage proportional to the concentration of a particular analyte of interest in a fluid sample in contact with film 200. In some embodiments, the signal from output beam 102 after passing through ICE 210 may be proportional to a property of interest of the fluid in contact with film 200. For example, the property of interest may be an octane rating and the fluid may be a gasoline sample including different types of gasoline.

Figure 3:
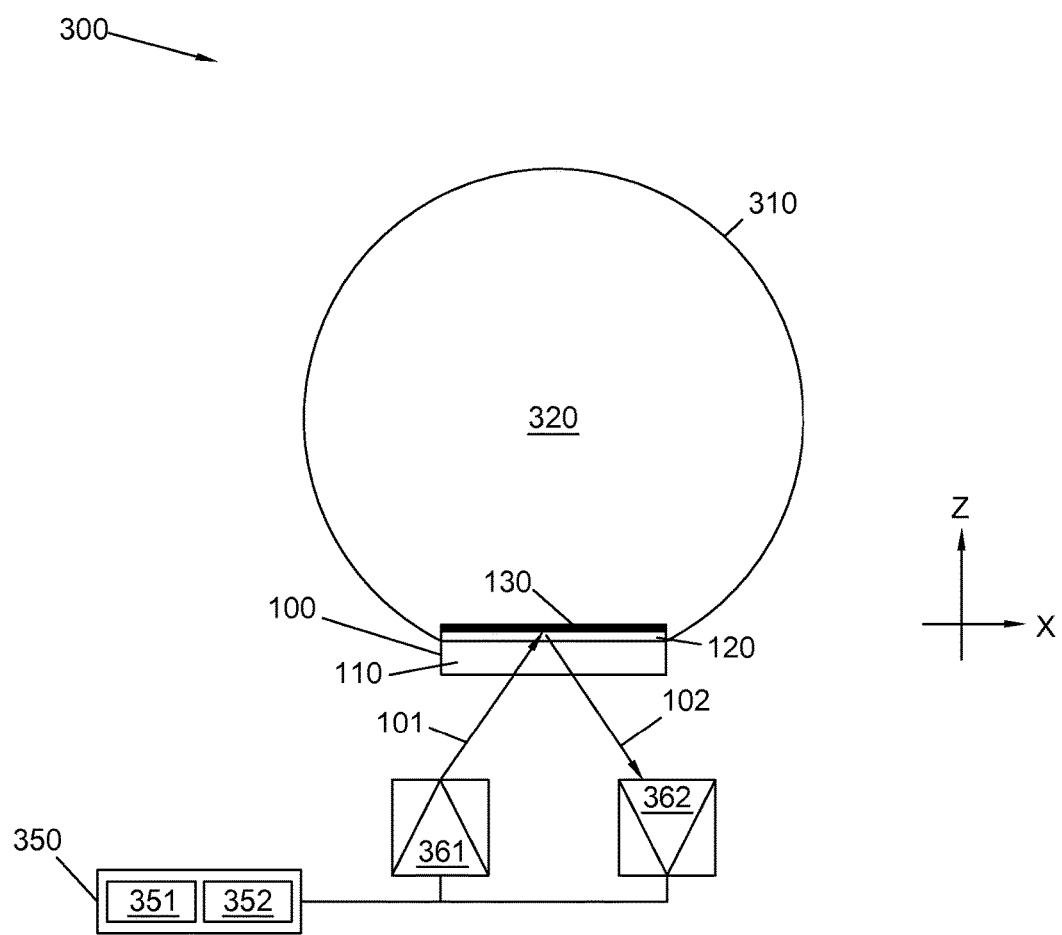
FIG. 3 shows a system using a multilayered film for measuring optically thick fluids in a fluid pipeline, according to some embodiments.

FIG. 3 shows a system 300 using multilayered film 100 for measuring optically thick fluids in a fluid pipeline 310, according to some embodiments. Fluid pipeline 310 includes optically thick fluid 320. System 300 includes film 100 having substrate 110, porous layer 120, and reflective layer 130, described in detail above (cf. FIG. 1). Setup 300 may also include an optical light source system 361 providing input beam 101, and an optical detector system 362 receiving reflected output beam 102. According to some embodiments, light source optical system 361 and detector optical system 362 may be controlled by controller 350. Controller 350 includes a processor circuit 351 and a memory circuit 352. Controller 350 is configured to turn 'on' and 'off' a light source in light source optical system 361. Controller 350 may be configured to collect, amplify, communicate and store the signal produced by reflected output beam 102 in detector optical system 362.

As illustrated in FIG. 3, multilayer film 100 is used in a reflection arrangement. Light source optical system 361 may include a light source such as a lamp, a laser, a tunable laser, or a light emitting diode. Light source optical system 361 may also include lenses, mirrors, optical filters and optical fibers to direct input beam 101 towards multilayered film 100. Output beam 102 reflected from multilayered film 100 is collected by detector optical system 362. Detector optical system 362 may include optical elements such as lenses, mirrors, optical filters, and optical fibers. Detector optical system 362 also includes at least one photo-detector to measure the intensity of output beam 102 ($I_{out}$). The photo-detector in detector optical system 362 provides a current or a voltage proportional to $I_{out}$. The current or voltage from the photo-detector is provided by detector optical system 362 to controller 350, for signal processing. Controller 350 may include an amplifier circuit to amplify the signal from detector optical system 362. Controller 350 may also include an analogue-to-digital converter circuit, to provide a digital signal from the signal collected at detector optical system 362.

Light source optical system 361 or detector optical system 362 may include a spectrometer (scanning monochromator, Fourier-transformed infrared or Fourier-transformed near-infrared) to allow the acquisition of a spectrum of fluid 320 in pipe 310.

FIG. 3 shows a cross-sectional view of flow pipe 310 with multilayered film 100 placed along a side. Fluid 320 may be stationary, or may be flowing, for example in a direction perpendicular to the cross sectional plane of FIG. 3 (Y-axis, not shown). The reflection configuration in system 300 allows measurements of large fluid flow rates due to the minimal penetration of multilayered film 100 into the bulk fluid 320. Thus, embodiments consistent with system 300 reduce the potential for restricting or perturbing the flow rate of fluid 320. Fluid 320 fills pores 140 in porous layer 120 of multilayered film 100 through a diffusion process having a speed that may vary according to the pore length $d_1$ and diameter $d_3$. In general, the filling of porous layer 120 occurs in a time period that allows collecting optical measurements as fluid 320 progresses along flow pipe 310. For example, for a porous layer 120 having diameters d3 from about 70 nm to about 100 nm and lengths $d_1$ of about 700 nm to about 750 nm, a filling time for more than 90% of porous layer 120 may be about 0.6 milliseconds (1 ms=0.001 seconds). Thus, according to some embodiments the fluid response time of porous layer 120 may be less than one (1) ms. In some embodiments, a fluid filling time may be shortened by applying a voltage through multilayered film 100, as will be described in detail below, in relation to FIGS. 4A and 4B.

Figure 4A:
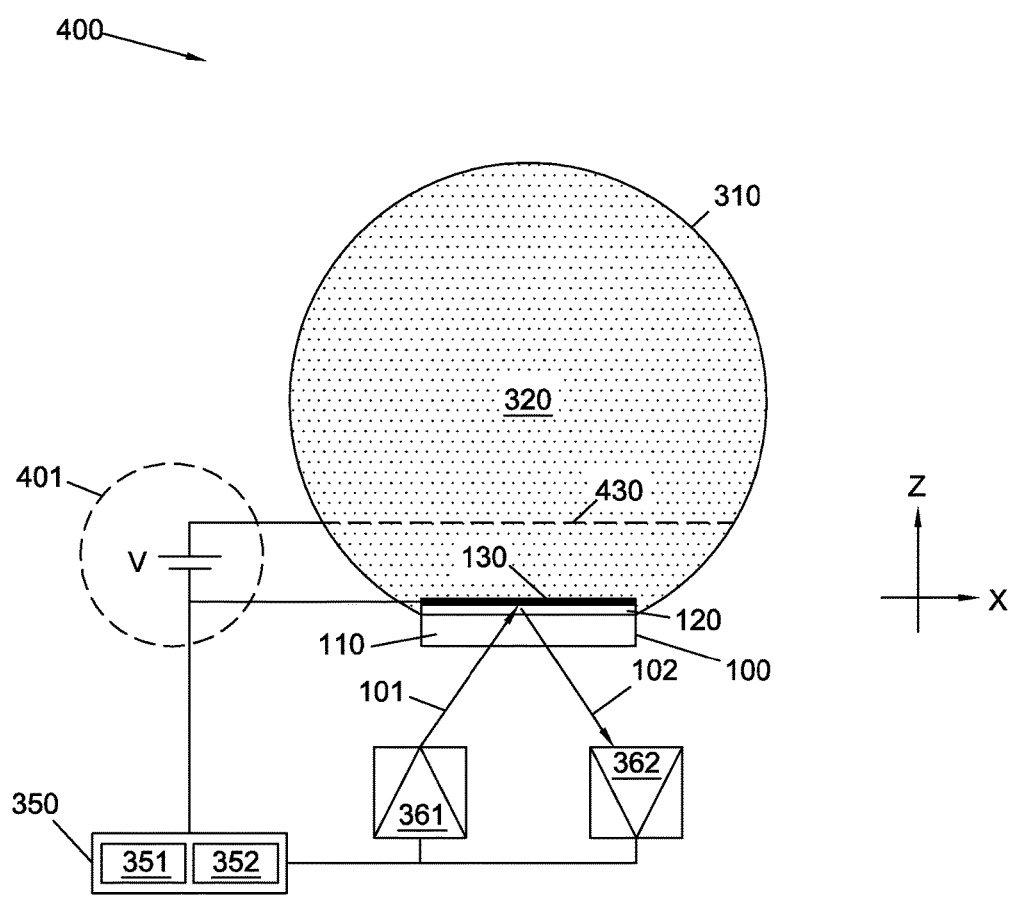
FIG. 4A shows a system using a multilayered film and a voltage circuit for measuring optically thick fluids in a fluid pipeline, according to some embodiments.

FIG. 4A shows a system 400 using multilayered film 100 and a voltage circuit 401 for measuring optically thick fluids in a fluid pipeline 310, according to some embodiments. Fluid pipeline 310 includes optically thick fluid 320. System 400 includes film 100, light source optical system 361, detector optical system 362, and controller 350 described in detail above (cf. FIG. 3). According to some embodiments, controller 350 may also control voltage circuit 401. System 400 includes an electrode 430 coupled to a first terminal in voltage circuit 401. In some embodiments electrode 430 is immersed in fluid 320. A second terminal in voltage circuit 401 may be coupled to reflective layer 130 in film 100. Accordingly, in some embodiments reflective layer 130 includes a conductive metal such as gold or aluminum, allowing a current to flow through circuit 401.

Figure 4B:
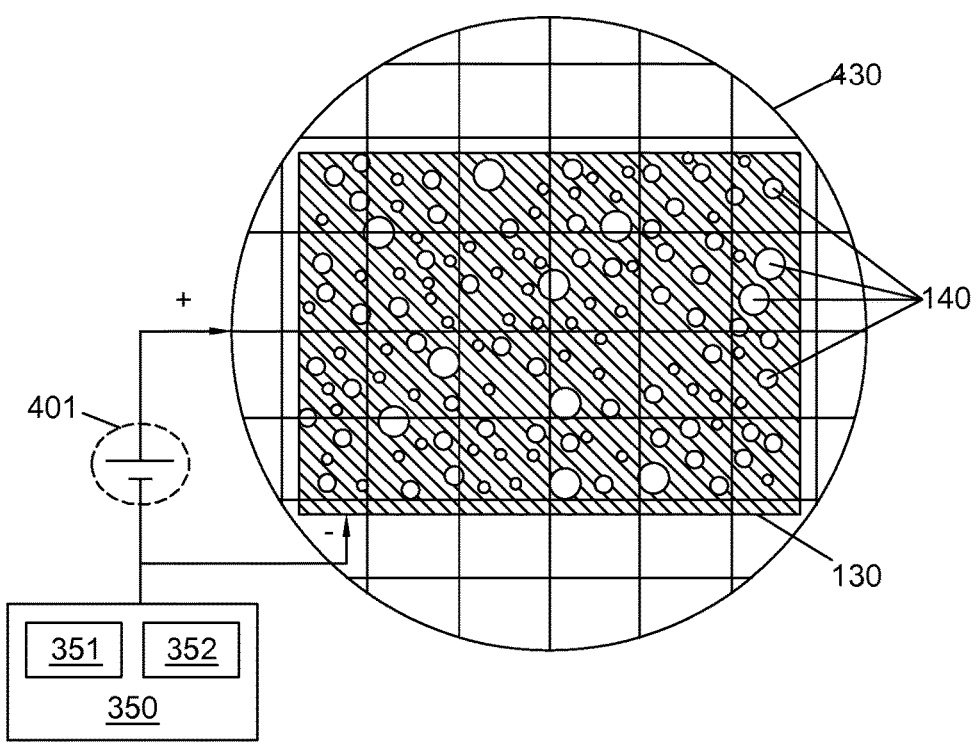
FIG. 4B shows a partial top view of a system using a multilayered film and a voltage circuit for measuring optically thick fluids in a fluid pipeline, according to some embodiments

FIG. 4B shows a partial top view of system 400, with electrode 430 coupled to a positive lead in voltage circuit 401. Reflective layer 130 is coupled to a negative lead in voltage circuit 401. As an electric field is established within fluid 320, positive electrolytes may be displaced toward pores 140, where a light source optical system and a detector optical system are able to detect and quantify the electrolyte amount. The selection of a positive lead in contact with electrode 430 and a negative lead in contact with reflective layer 130 is not limiting. One of ordinary skill would recognize that the opposite configuration is possible, with a negative lead in contact with electrode 430, and a positive lead in contact with reflective layer 130. In such configuration, a negative electrolyte may be displaced toward pores 140, to be measured by a light source optical system and a detector optical system.

Heat generated resistively by the current flow through reflective layer 130 removes residual fluid in porous layer 120 after an optical measurement. Thus, the fluid re-filling speed of multilayered film 100 may be increased, particularly in the case of dense fluids filling the pores. In some embodiments voltage V may produce electrolysis of electrolytes dissolved in fluid 320. A redox reaction in the fluid may thus be monitored by measuring different ions collected within porous layer 120. In some embodiments, a system 400 may be combined with standard electrochemical techniques to conduct measurements on charged chemical species, or their byproducts. This may be useful in oil industry applications such as oil refining, gas and gasoline production, and distribution.

Figure 5:
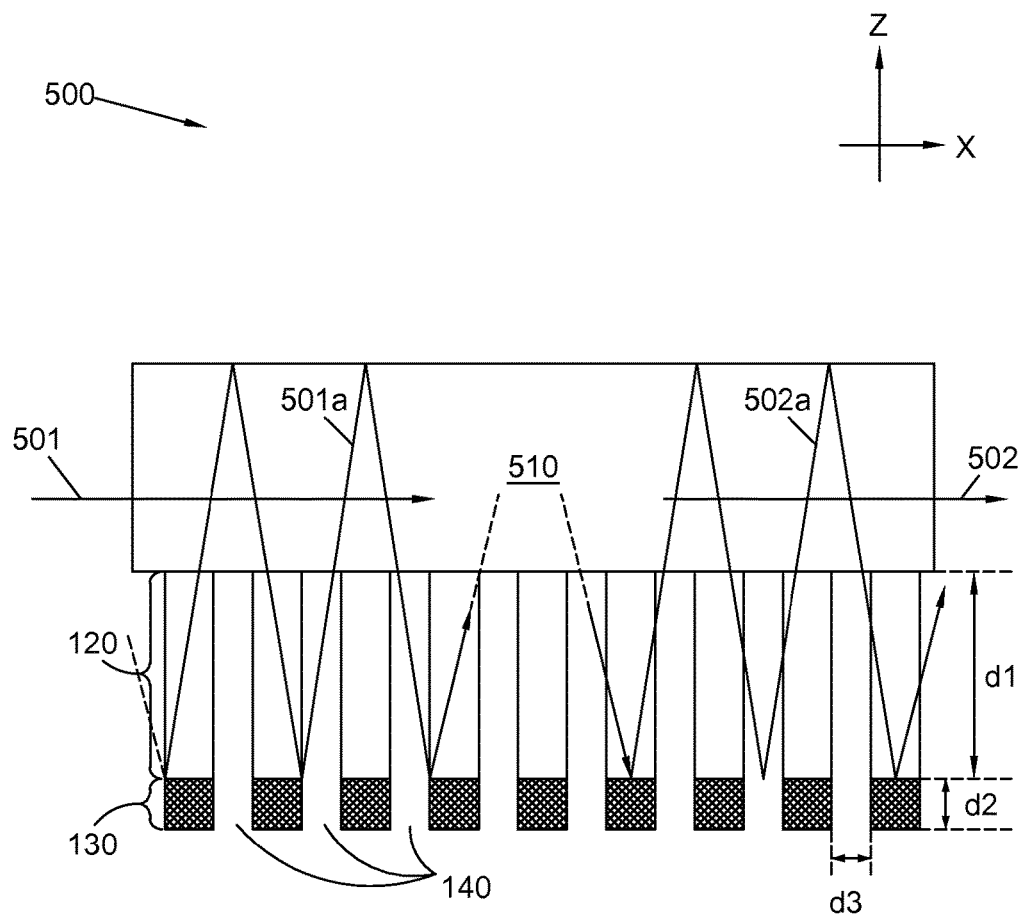
FIG. 5 shows a multilayered film waveguide for measuring optically thick fluids, according to some embodiments.

FIG. 5 shows a multilayered film waveguide 500 for measuring optically thick fluids, according to some embodiments. Film waveguide 500 may include a waveguide substrate 510, porous layer 120 having pores 140, and reflective layer 130. Porous layer 120 and reflective layer 130 are as described in detail above (cf. FIG. 1). Waveguide 510 supports an input propagating mode 501 and an output propagating mode 502. According to embodiments consistent with the present disclosure, output propagating mode 502 may be determined by the optical properties of porous layer 120, which in turn depend on the type of fluid and particles filling pores 140. For example, in some embodiments, the propagation constant of output propagating mode 502 may depend on the refractive index of porous layer 120. The refractive index of porous layer 120 may depend on the chemical composition of the fluid filling pores 140. For example, when the fluid filling pores 140 absorbs a portion of input propagating mode 501, the refractive index of a propagating beam may have an imaginary component. An imaginary component of the refractive index attenuates the amplitude of output propagating mode 502 at selected wavelengths. In some embodiments, a fluid may affect a real component of the refractive index of input propagating mode 501, thus affecting the coupling of output propagating mode 502 into waveguide 510.

In some embodiments, waveguide 510 acts as a total internal reflector which, when combined with reflective layer 130 produces multiple reflections 501a of an input propagating mode 501. Thus, output propagating mode 502 has a reduced amplitude, according to absorption by a given analyte filtered through pores 140 into porous layer 120.

Figure 6:
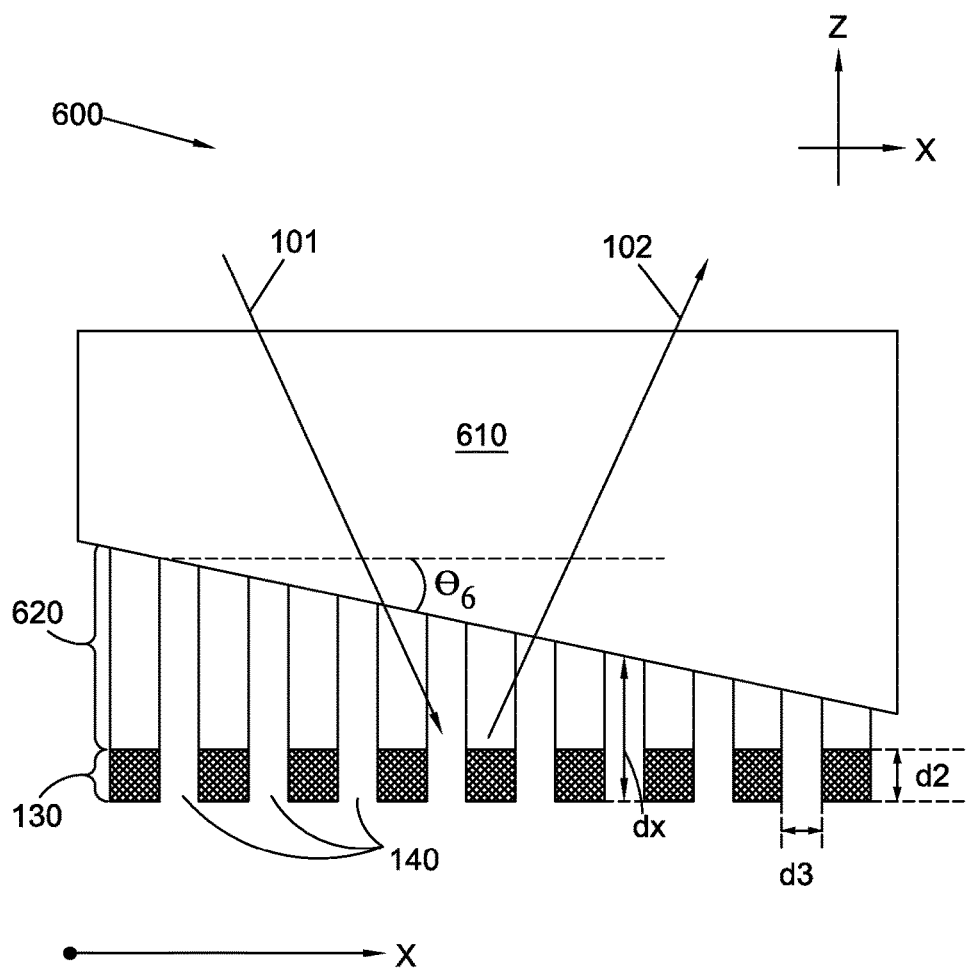
FIG. 6 shows a wedged multilayered film for measuring optically thick fluids, according to some embodiments.

FIG. 6 shows a wedged multilayered film 600 for measuring optically thick fluids, according to some embodiments. Film 600 includes an optically transparent substrate layer 610 having a wedge shape. Film 600 also includes porous layer 620 having a wedge shape, with reflective layer 130 deposited on a surface of porous layer 620. According to some embodiments, the wedges formed by substrate layer 610 and porous layer 620 are complementary, so that reflective layer 130 is substantially parallel to the upper surface of substrate layer 610.

The wedge-shape in porous layer 620 has a thickness dx that is variable along the X-direction. In some embodiment thickness dx may be a linear function of the distance 'x'. For example, a surface of porous layer 620 adjacent to a surface in substrate layer 610 may form an angle $\theta_6$. Angle $\theta_6$, for example, may range from 10-45 degrees. One of ordinary skill would recognize that the functional form of thickness 'dx' is not limiting. The functional form of thickness 'dx' may be chosen according to a desired result for the absorbance of input beam 101 as measured by output beam 102. For example, in some embodiments the shape of the wedge formed by porous layer 620 may be curved following a logarithmic function. Thus, the absorbance A for a portion of film 600 traversed by input beam 101 and output beam 102 may be substantially a linear function of the ratio between $I_{in}$ and $I_{out}$ (cf. Eq.(5), above).

In some embodiments it is desirable that the absorbance $A(\lambda)$ (cf. Eq.(2)) be approximately proportional to $1/T_\lambda$ for a broader range of values than 0.1 or less (cf. Eq.(5)). In such configuration, an analyte concentration value may be proportional to a signal provided by detector optical system 362 for a wide range of values of '$I_{out}$'. In some embodiments, it is desirable that the absorbance $A(\lambda)$ be approximately proportional to $1/T_\lambda$ for values of '$I_{out}$' in a linear range of operation of detector optical system 362 (cf. FIG. 3).

To achieve linearity, some embodiments use wedged multilayer film 600, combined with an input beam 101 and an output beam 102 having a broad cross section. The reflected output beam 102 is then collected by the photodetector in detector optical system 361 by using a focusing lens or a focusing optical element, to concentrate all the light from output beam 102 onto a single photo-detector. Thus, the photo-detector effectively performs a spatial integration of output beam 102 along a plurality optical path lengths given by the portion of values dx covered by the broad input beam 101. As a result, the integrated output signal, $I_{out}$, and the integrated input signal, $I_{in}$, may have a linear dependence with absorbance $A(\lambda)$, for a wide range of values of $A(\lambda)$.

According to some embodiments, linearity may be obtained with wedged multilayer film 600, input beam 101 and output beam 102 having negligible cross-sections, as follows. Scanning input beam 101 along the X-direction to cover a range of values dx, the signal detected from output beam 102 may be integrated for the duration of the scan. The result of the integral will include output intensities across a range of optical path values dx. The result is then analogous to spatial integration of a broad input beam 101. Thus, a linear relation for a broad absorbance range is obtained.

In some embodiments, the linear range of absorbance provided by wedged porous layer 620 may encompass several decades of a logarithmic scale. Thus, for example, thickness dx may be designed so that a linear relation for $1/T_2$ may be obtained for an OD from about 0, up to about 30. Multilayered film 600 having wedged porous layer 620 may increase the dynamic range of optical densities for spectroscopic measurements in optically thick fluids. For example, an optically thick fluid may include a first analyte with high absorbance $A_1(\lambda)$, and a second analyte with low absorbance $A_2(\pi)$. When the value of $1/T_\lambda$ is linear with respect to absorbance, both absorbance $A_1(\lambda)$ and absorbance $A_2(\lambda)$ may be measurable within the detection range for $I_{out}$ of detector optical system 362.

Accordingly, the first analyte $(A_1(\lambda))$ may best be measured for portions of input beam 101 traversing pores having a shorter length, and the second analyte $(A_2(\lambda))$ may best be measured for portions of input beam 101 traversing pores having a longer length. By having input beam 101 broad enough to cover shorter and longer pores, an optimized measurement may be obtained for the first analyte and the second analyte. In some embodiments, scanning input beam 101 along short and long pores results in an optimized measurement for the first analyte and the second analyte. Embodiments consistent with wedged multilayered film 600 may also be desirable to suppress etalon fringes in wedge substrate 610, typically occurring for optical interfaces having planar configurations.

Figure 7:
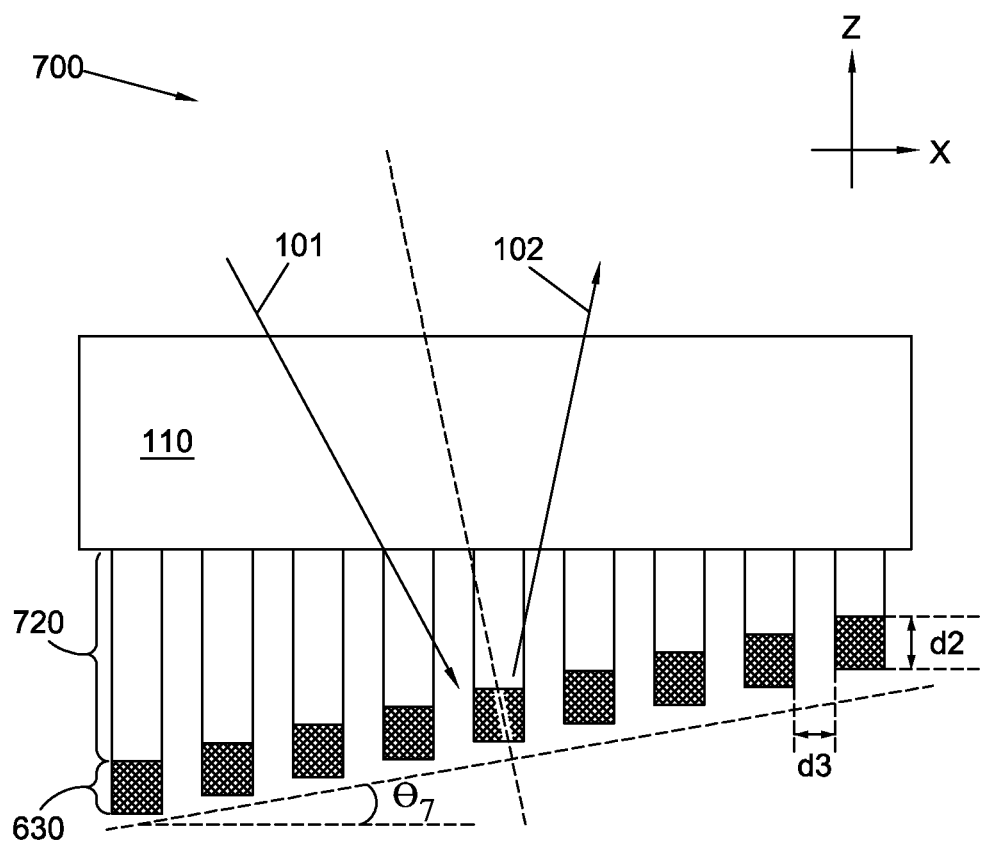
FIG. 7 shows a wedged multilayered film for measuring optically thick fluids, according to some embodiments.

FIG. 7 shows a wedged multilayered film 700 for measuring optically thick fluids, according to some embodiments. Film 700 includes an optically transparent substrate layer 110 having a flat shape. Film 700 also includes porous layer 720 having a wedge shape, with reflective layer 130 deposited on a surface of porous layer 720. According to some embodiments, the wedge formed by porous layer 720 next to flat substrate layer 110 results in a wedged film 700. Thus, reflective layer 130 may form an angle $\theta_7$ with the upper surface of substrate layer 110. Angle $\theta_7$, for example, may range from 10-45 degrees.

According to some embodiments, a linear measurement may be obtained using wedged multilayered film 700 with a spatial integration or a scanning beam approach, as described in detail above (cf. FIG. 6). Embodiments of measurement configurations using a wedged multilayered film as film 700 are desirable with a multilayered film waveguide as described in detail above (cf. FIG. 5). Thus, optically transparent substrate 110 in wedged multilayered film 700 may form a waveguide such as waveguide 510. In such embodiments, output propagation mode 502 may include an integrated effect of different optical paths dx, along the waveguide direction (X-axis). In such embodiments a linear relation for $1/T_\lambda$ may be obtained for a wide range of absorbance values.

Figure 8:
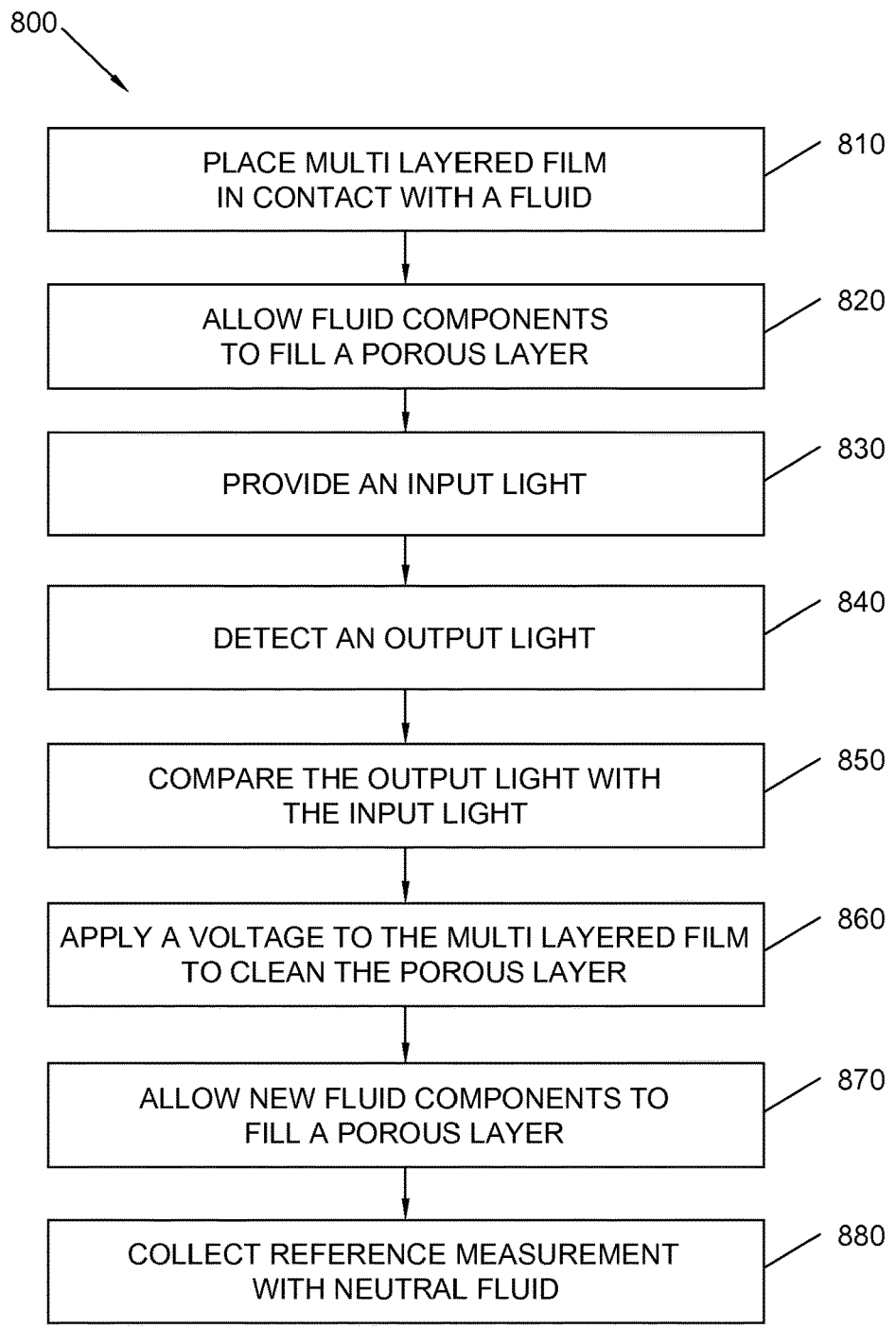
FIG. 8 shows a flowchart for a method to measure optically thick fluids, according to some embodiments.

FIG. 8 shows a flowchart for a method 800 to measure optically thick fluids, according to some embodiments. In step 810 a multilayered film is placed in contact with a fluid. The multilayered film may be as multilayered film 100, including optically transparent substrate 110, porous layer 120, and reflective layer 130 (cf. FIG. 1). In some embodiments, the fluid may be as fluid 320 stationary or flowing in a container or conduit such as flow pipe 310 (cf. FIG. 3). In step 820 fluid components are allowed to fill pores in a porous layer in the multilayered reflector. In step 830 an input light is provided. In some embodiments, step 830 may include directing an input light through the substrate layer in a multilayered film as disclosed herein. The input light may be an optical beam as input beam 101 (cf. FIG. 1) or a propagating mode as input propagating mode 501 in multilayered film waveguide 500 (cf. FIG. 5). In some embodiments step 830 is performed with light source optical system 361 (cf. FIG. 3). In step 840 an output light is detected. The output light detected in step 840 may be output beam 102 reflected off of a reflective layer in multilayered film in step 810 (cf. FIG. 1). In some embodiments, the output light detected in step 840 may be output propagating beam 502 in multilayered film waveguide 500 (cf. FIG. 5). Further according to some embodiments, step 840 is performed with a detector optical system such as system 362 (cf. FIG. 3).

In step 850 the output light is compared to the input light. In some embodiments, step 850 is performed by providing a signal to a controller circuit such as controller 350 (cf. FIG. 3). The signal may be provided by detector optical system 362 in step 840. Processor circuit 351 in controller 350 may perform logic operations comparing an input light intensity provided by system 361 to an output light intensity measured by system 362. Furthermore, in some embodiments processor circuit 351 may compute a value $1/T_\lambda$ and obtain a value for $A(\lambda)$. Having parameters such as $\varepsilon(\lambda)$ and $I(\lambda)$ stored in memory circuit 352, a value for the analyte concentration C may be obtained from $A(\lambda)$, in step 850 (cf. Eq.(2)).

In step 860 a voltage is applied to the multilayered film to clean the pores in the porous layer. In some embodiments, the voltage is applied by a controller circuit such as controller 350 to a circuit such as circuit 401 (cf. FIG. 4). The voltage may induce a current flow through the multilayered film, resistively heating the reflective layer and the porous layer, thus removing the fluid that has already been measured according to steps 820-850. In step 870 new fluid components are allowed to fill the pores in the porous layer. Thus, when step 870 is completed, method 800 may be repeated for a subsequent measurement of the optically thick fluid. In some embodiments, method 800 includes step 880 to collect a reference measurement with the multilayered film using a neutral fluid. A neutral fluid may be a fluid that has no absorption features in the spectral region of interest. A neutral fluid may also include a fluid having an index of refraction equal or substantially similar to the index of refraction of the porous layer in the multilayered film. Step 880 may include measuring the scattering effects produced by the pore features in the reflective layer on output beam 102. Since the scattering effects produced by the pores in the reflective layer are independent of the absorption properties of the fluid in the porous layer, step 880 may be used to remove the scattering effects from measurements in the optically thick fluid.

Figure 9:
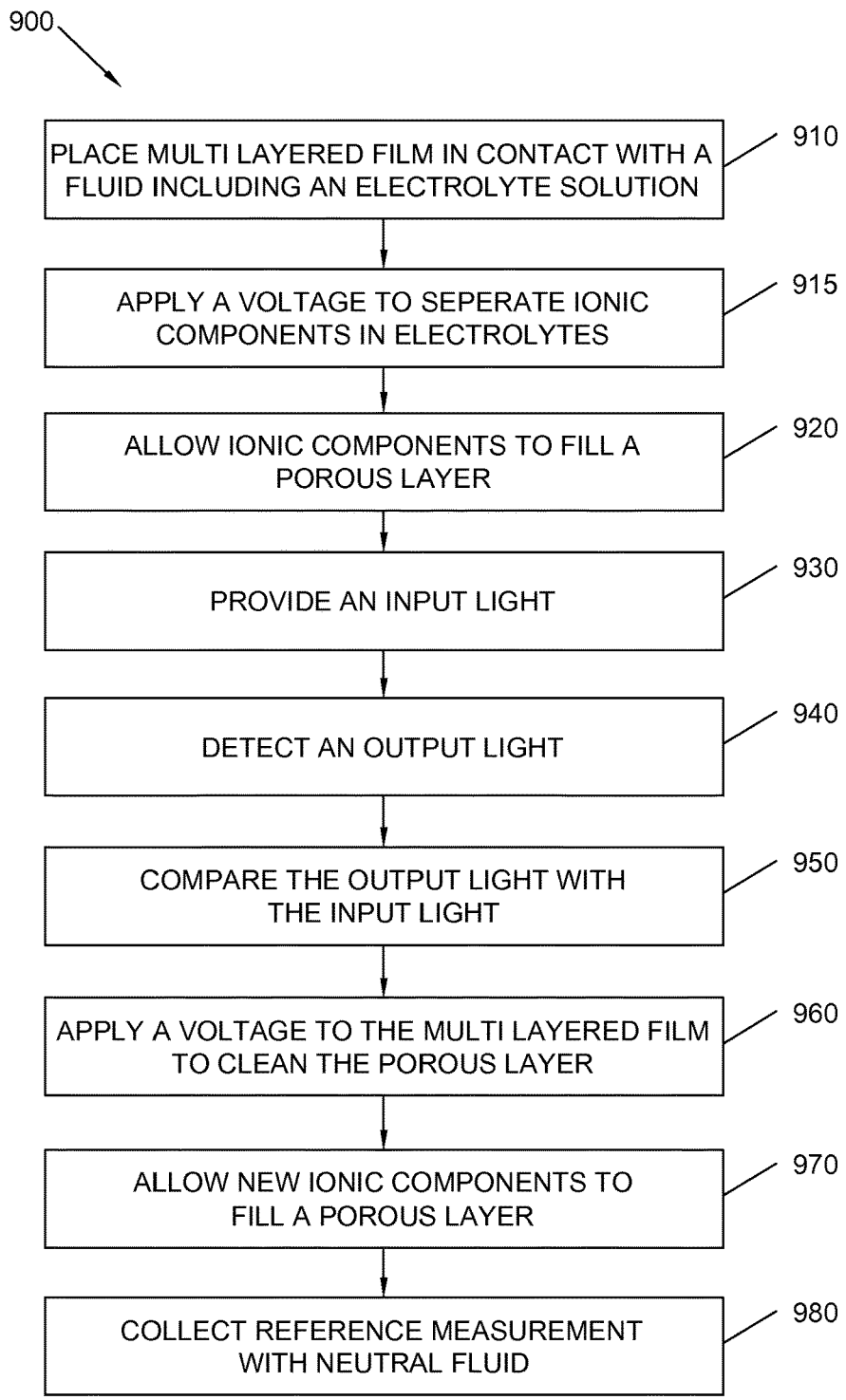
FIG. 9 shows a flowchart for a method to measure optically thick fluids, according to some embodiments.

FIG. 9 shows a flowchart for a method 900 to measure optically thick fluids, according to some embodiments. Method 900 includes step 910 as step 810 described in detail above (cf. FIG. 8). In some embodiments, the fluid in step 910 includes an electrolyte solution. In step 915 a voltage 'V' is applied to the multilayered film to separate ionic components in electrolytes forming the electrolyte solution in the fluid. In step 920 the ionic components separated in step 915 are allowed to fill the pores in a porous layer of the multilayered film. Steps 930, 940, 950, 960, 970, and 980 are as steps 830, 840, 850, 860, 870, and 880, respectively, described in detail above (cf. FIG. 8).

Figure 10:
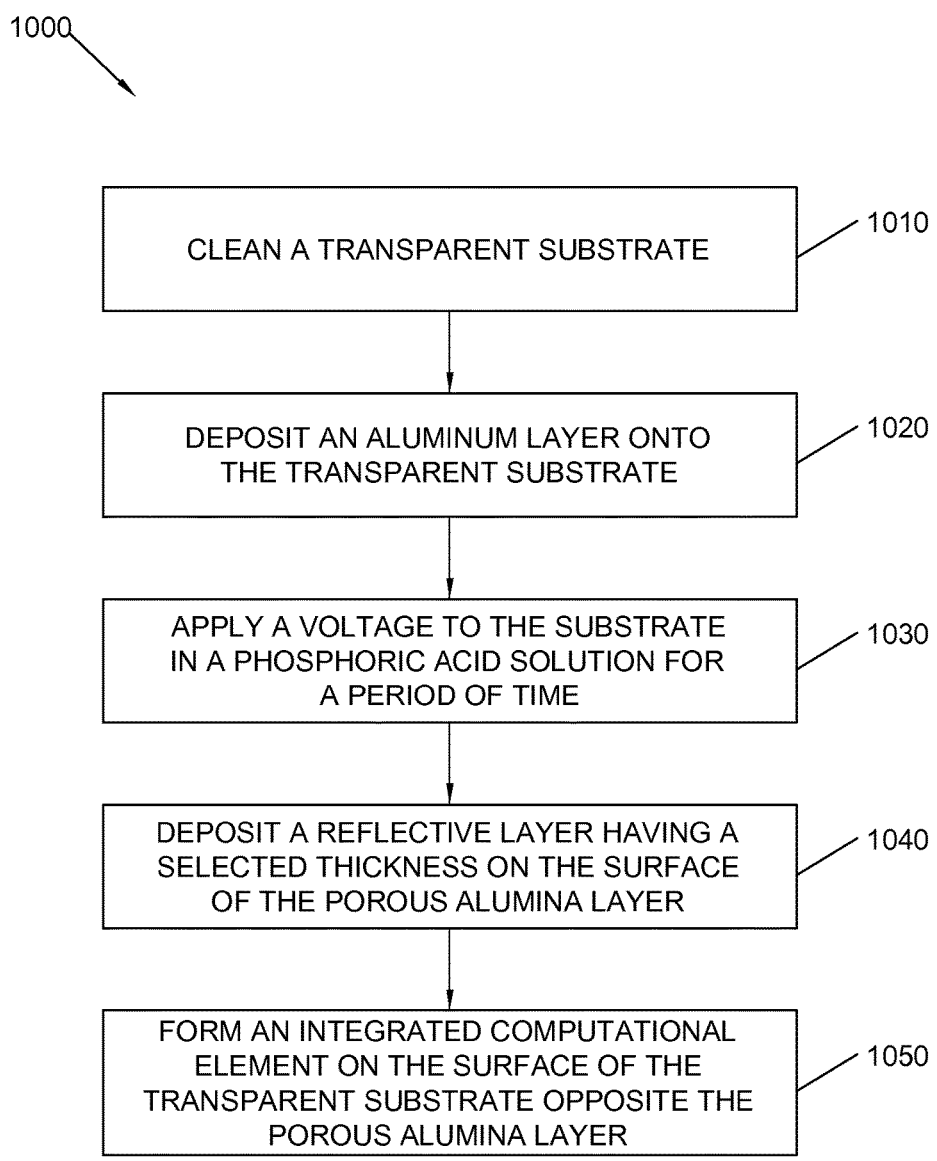
FIG. 10 shows a flowchart for a method of manufacturing a multilayered film for measuring an optically thick fluid, according to some embodiments.

FIG. 10 shows a flowchart for a method 1000 of manufacturing a multilayered film for measuring an optically thick fluid, according to some embodiments. The multilayered film resulting from method 1000 may be as multilayered film 100, described in detail above (cf. FIG. 1). In step 1010 a transparent substrate is cleaned. The transparent substrate in step 1010 may be as transparent substrate 110 described in detail above (cf. FIG. 1). In some embodiments, step 1010 includes a piranha etch using a 3:1 solution of sulfuric acid and 30% hydrogen peroxide. When etching is completed, the transparent substrate may be rinsed with de-ionized water. In step 1020 an aluminum layer is deposited onto the transparent substrate prepared in step 1010. The aluminum layer is used to form a porous layer such as porous layer 120 (cf. FIG. 1). For example, substrate 110 may be made of a sapphire slab, according to some embodiments. The thickness of the aluminum layer deposited on the transparent substrate is controlled so that the resulting porous alumina film is of the appropriate thickness to control the overall path length needed to make an optical measurement of a fluid (cf. d1 in FIG. 1).

In step 1030 a voltage is applied to the aluminum layer in a phosphoric acid solution, for a period of time. The result is oxidation of substantially all the aluminum layer, forming a porous layer of alumina ($AlO_3$) having pores of length $d_1$ and diameter $d_3$ (cf. FIG. 1). In some embodiments step 1030 includes anodization of the aluminum into porous alumina. The resulting porous alumina film from step 1030 has a thickness approximately 150% of the original thickness of the aluminum layer. This results from incorporating oxygen in aluminum's crystal structure. Thus, in some embodiments the thickness of the porous alumina layer may be determined by selecting the thickness of the original aluminum layer deposited in step 1030. Therefore, the optical path length of a multilayered film consistent with the present disclosure may be controlled to within a few nanometers. In some embodiments, step 1030 may include measuring a thickness $d_1$ of the porous alumina layer, and an average pore diameter $d_3$. A measurement of $d_1$ and $d_3$ may be performed by using a transmission electron microscope (TEM) image of the porous alumina layer. One of ordinary skill will recognize that other standard techniques may be used to measure $d_1$ and $d_3$, such as conventional optical microscopy and other techniques well known in the art.

In step 1040 a reflective layer is deposited on the surface of the porous alumina layer. The reflective layer has a selected thickness $d_2$ (cf. FIG. 1). A large pore diameter d3 allows for filling of the porous layer with fluid components in a short time. A small diameter $d_3$ of the pores filters out suspended particles that may interfere with optical measurements, like asphaltenes in crude oil.

In some embodiments step 1040 may include sputtering a conducting material such as gold on the porous alumina layer. Step 1040 is performed such that the ends of the pores formed in the porous alumina layer are not sealed by the reflective layer. The diameter of the pores may be selected to be smaller than the wavelength of light used for spectroscopy, including the UV region of the electromagnetic spectrum ($\lambda$=400 nm or less, cf. $d_3$ in FIG. 1). Thus, the reflecting coating layer acts as a seamless reflector for light having a wavelength from the UV to the near-infrared, and mid infrared wavelength regions. In some embodiments, method 1000 may include step 1050 where an integrated computational element (ICE) may be formed on the surface of the optically transparent layer, opposite the porous alumina layer. An ICE deposited on the multilayer film may be as ICE 210 in film 200 (cf. FIG. 2). Accordingly, step 1050 may be performed on any one of the embodiments consistent with the present disclosure, as previously described. For example, step 1050 may be performed by forming an ICE on multilayered film waveguide 500. In some embodiments, step 1050 may include forming an ICE on wedged multilayered film 600. Further according to some embodiments, step 1050 may include forming an ICE on wedged multilayered film 700.

Figure 11:
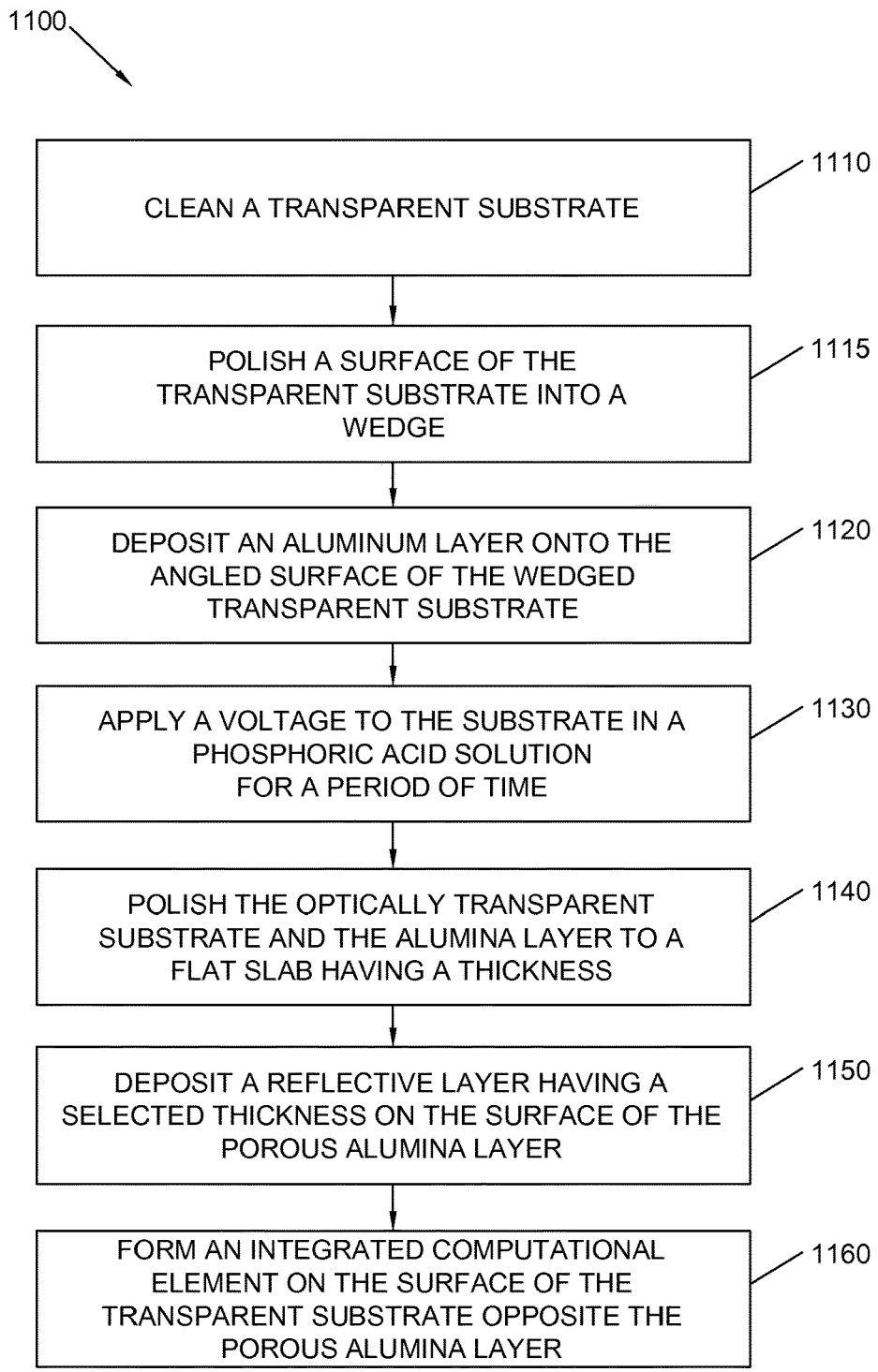
FIG. 11 shows a flowchart for a method of manufacturing a multilayered film for measuring an optically thick fluid, according to some embodiments.

FIG. 11 shows a flowchart for a method 1100 of manufacturing a multilayered film for measuring an optically thick fluid, according to some embodiments. Steps 1110, 1120, 1130, 1140, and 1150 are similar to steps 1010, 1020, 1030, 1040, and 1050 described in detail above (cf. FIG. 10). In step 1115 a surface of the transparent substrate in step 1110 is polished into a wedge. In step 1135 the transparent substrate and the alumina layer resulting from step 1130 are polished to form a flat slab having a thickness. Thus, in some embodiments the multilayered film resulting from method 1100 may be such as wedged multilayered film 600 (cf. FIG. 6).

Figure 12:
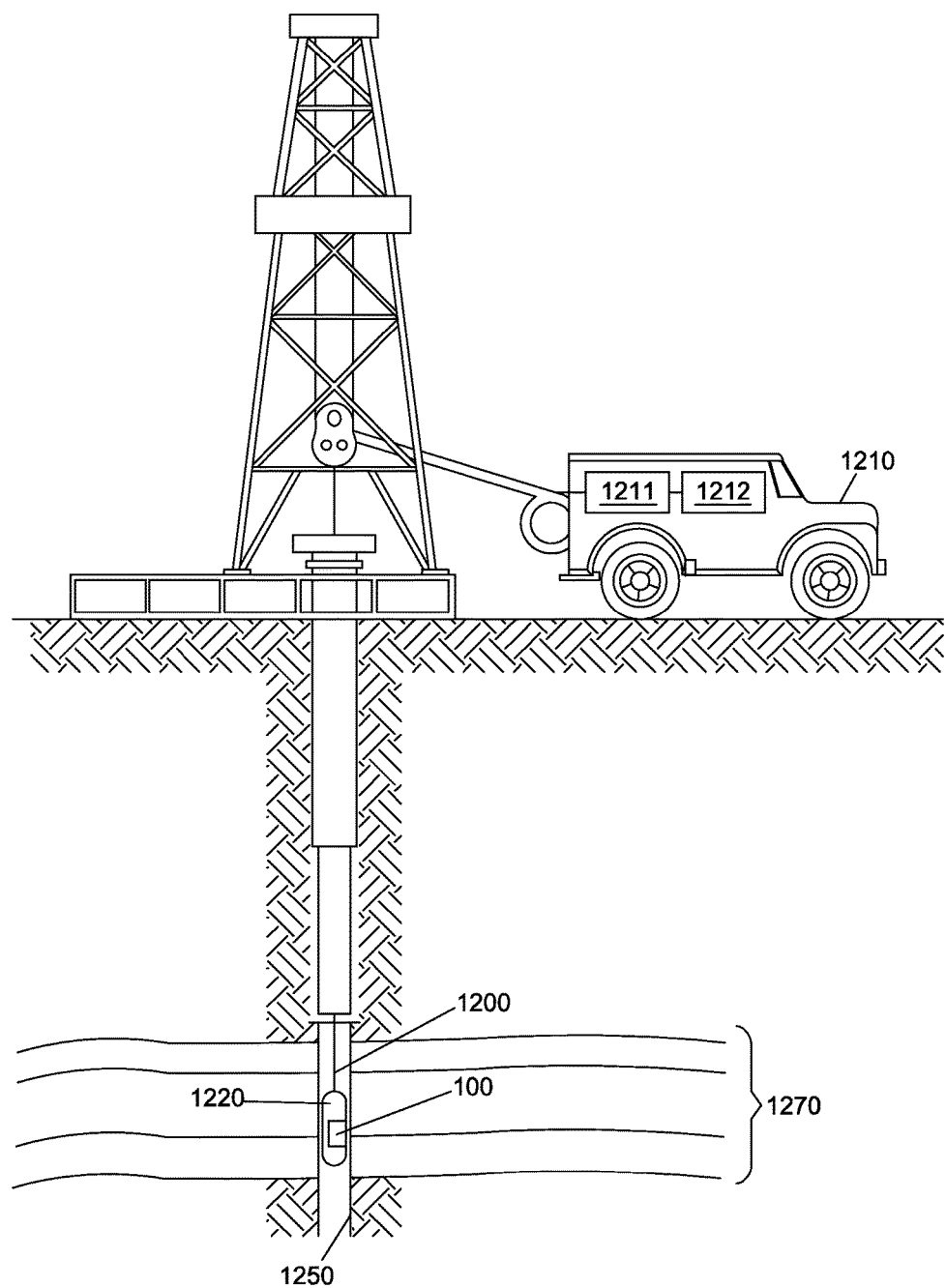
FIG. 12 shows a sensor using a multilayered film for measuring an optically thick fluid in a wireline logging application, according to some embodiments.

FIG. 12 shows a sensor 1220 using multilayered film 100 for measuring an optically thick fluid in a wireline logging application, according to some embodiments. Wireline logging performs measurements of fluids and substrates in wellbores drilled for oil and hydrocarbon exploration. In some embodiments, a movable unit 1210 includes a processor circuit 1211 and a memory circuit 1212 to provide commands for sensor 1220 to perform measurements and store data obtained from the measurements. Accordingly, once a wellbore 1250 has been drilled, a wireline logging measurement may be performed by introducing sensor 1220 into wellbore 1250, using a wireline 1200. Wellbore 1250 may traverse a ground formation 1270. Sensor 1220 may have an optical sensor system including multilayered film 100, as disclosed herein. Furthermore, sensor 1220 may include a portion of a light illumination system such as light illumination system 361 and a portion of a light detection system such as light detection system 362 (cf. FIG. 3). In some embodiments, a portion of light illumination system 361 may be included in movable unit 1210, such as a laser device, or an illumination lamp. Likewise, a portion of light detection system 362 may be included in movable unit 1210, such as a detector, an amplifier, and an analog-to-digital converter circuit. In some embodiments, light illumination system 361 and light detection system 362 may include an optical fiber, or fiber bundle. The optical fiber or fiber bundle carries light signals along wireline 1200.

Figure 13:
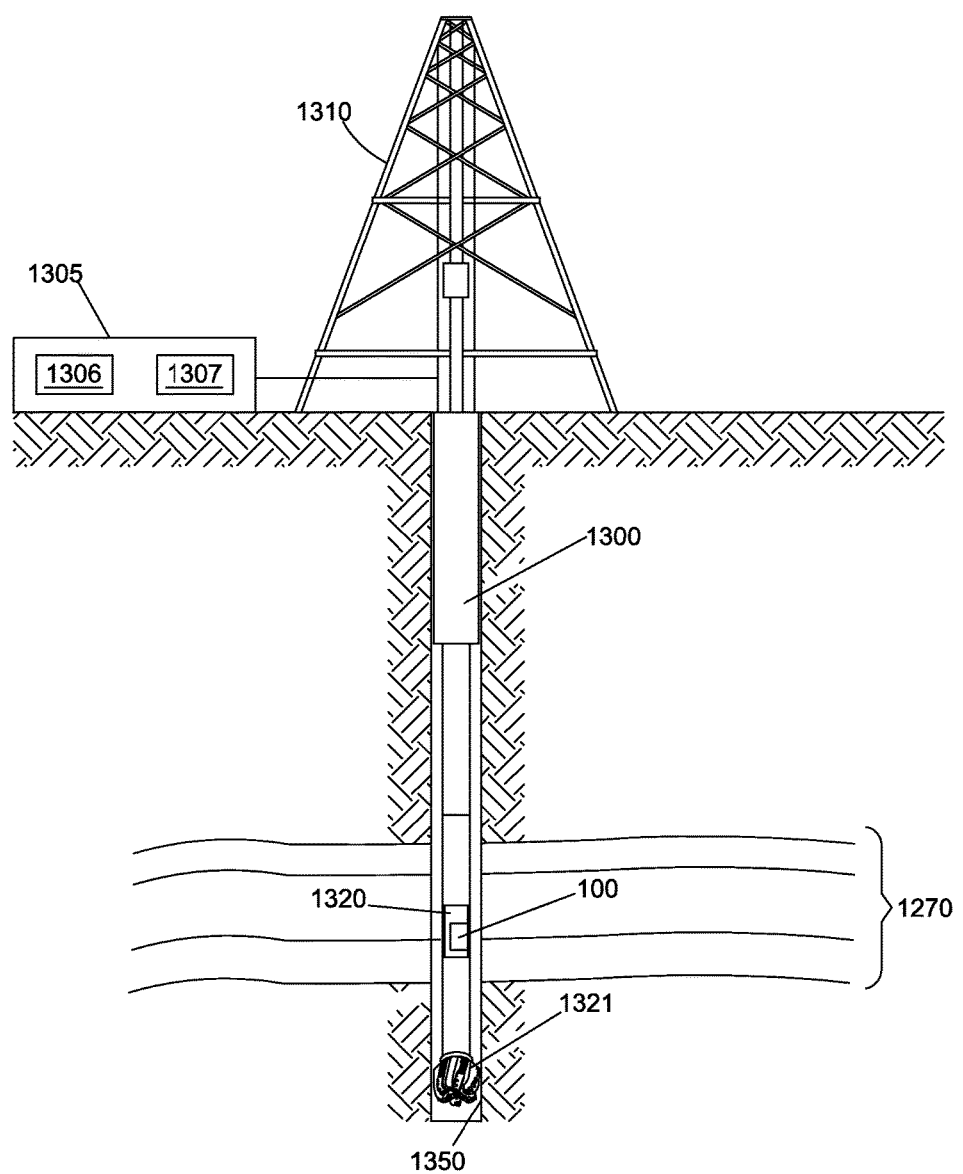
FIG. 13 shows a drill bore including a sensor having a multilayered film for measuring an optically thick fluid in a logging-while-drilling (LWD) application, according to some embodiments.

FIG. 13 shows a drill bore including a sensor 1220 having a multilayered film 100 for measuring an optically thick fluid in a logging-while-drilling (LWD) application, according to some embodiments. An LWD configuration logs acoustic data while a wellbore is being drilled. According to FIG. 13, a bottom hole assembly 1320 includes a drill 1321 to form a wellbore 1350. Wellbore 1350 may traverse a ground formation 1270. Drill 1321 may be operated by a controller 1305 through drill string 1300. A drilling rig 1310 provides structural support to drill string 1300. Controller 1305 may include a processor circuit 1306 and a memory circuit 1307. Memory circuit 1307 stores commands and data used by processor circuit 1306 to control bottom hole assembly 1320. Controller 1305 may also operate sensor 1220 included in drill 1320. Sensor 1220 may include multilayered film 100 for measuring an optically thick fluid in an LWD application. Sensor 1220 may also include a portion of a light illumination system and a portion of a light detection system, as described in detail above (cf. FIG. 12). Accordingly, in LWD applications as depicted in FIG. 13, sensor 1220 may transmit and receive data from controller 1305 using signals raveling through the drilling mud, or an acoustic telemetry device, or a wired pipe configuration.

In some embodiments, a sensor including a multilayered film as disclosed herein may be implemented in permanent monitoring applications. For example, in an oil extraction rig similar to drilling rig 1310, multilayered film 100 may determine the chemical composition of the extracted hydrocarbons during regular operations. Further according to some embodiments, an optical sensor including multilayered film 100 may be used in a subsea environment of a wireline operation (cf. FIG. 12), an LWD operation (cf. FIG. 13), or a permanent monitoring operation.

Embodiments described herein are exemplary only. One skilled in the art may recognize various alternative embodiments from those specifically disclosed. Those alternative embodiments are also intended to be within the scope of this disclosure. As such, the embodiments are limited only by the following claims.

What is claimed is:

1. A method for measuring properties of a fluid, the method comprising:
   directing an input light through a multivariate optical element (MOE) of a multilayered film, then through a substrate and a porous layer of the multilayered film, the multilayered film further including a reflective layer disposed on the porous layer, and the porous layer having the fluid therein;
   reflecting the input light using the reflective layer, thereby forming an output light which is directed back through the porous layer and the substrate, then through the MOE;
   detecting the output light from the multilayered film; and
   comparing the output light with the input light to measure a property of at least one component of the fluid.

2. The method of claim 1, wherein a plurality of pores in the porous layer excludes particulates and contaminants from filling interior portions of the pores, the excluded particulates and contaminants being larger in size than a diameter of the pores.

3. The method of claim 2, wherein the larger particulates and contaminants comprise asphaltenes.

4. A method for measuring properties of a fluid, the method comprising:
   directing an input light through a multilayered film, the multilayered film comprising a substrate, a multivariate optical element (MOE), a porous layer, and a reflective layer disposed on the porous layer;
   detecting an output light from the multilayered film;
   comparing the output light with the input light to measure a property of at least one component of the fluid; and
   resistively heating the reflective layer to allow cleaning of deposits from openings of the porous layer.

5. The method of claim 4, wherein a plurality of pores in the porous layer excludes particulates and contaminants from filling interior portions of the pores, the excluded particulates and contaminants being larger in size than a diameter of the pores.

6. The method of claim 5, wherein the larger particulates and contaminants comprise asphaltenes.

7. The method of claim 4, wherein the fluid comprises crude oil.

8. The method of claim 4, wherein the fluid is in a wellbore formed in a procedure selected from the group consisting of a wireline logging procedure and a logging while drilling (LWD) procedure.

9. The method of claim 4, wherein directing the input light through the multilayered film comprises:
   directing the input light through the MOE, then through the substrate and the porous layer having the fluid therein; and
   reflecting the input light using the reflective layer, thereby forming an output light which is directed back through the porous layer and the substrate, then through the MOE.

10. The method of claim 4, wherein the fluid comprises an electrolyte solution separable into ionic components, the method further comprising: applying a voltage to separate the ionic components; allowing at least one of the ionic components to fill the pores in the porous layer; and optically measuring the at least one ionic component filling the pores.

11. The method of claim 1, wherein the fluid comprises crude oil.

12. The method of claim 1, wherein the fluid comprises an electrolyte solution separable into ionic components, the method further comprising:

applying a voltage to separate the ionic components;
allowing at least one of the ionic components to fill the pores in the porous layer; and
optically measuring the at least one ionic component filling the pores.

13. The method of claim 1, wherein the fluid is in a wellbore formed in a procedure selected from the group consisting of a wireline logging procedure and a logging while drilling (LWD) procedure.

14. The method of claim 1, further comprising:
placing a side of the multilayered film in contact with the fluid such that the porous layer is filled with analytes of interest.

* * * * *